(12) United States Patent
Shabsigh

(10) Patent No.: US 6,706,682 B2
(45) Date of Patent: *Mar. 16, 2004

(54) USES OF VASCULAR ENDOTHELIAL GROWTH FACTOR IN THE TREATMENT OF ERECTILE DYSFUNCTION

(75) Inventor: Ridwan Shabsigh, Wayne, NJ (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/234,591

(22) Filed: Jan. 21, 1999

(65) Prior Publication Data

US 2003/0124094 A1 Jul. 3, 2003

(51) Int. Cl.[7] .................. A01N 37/18; A01N 37/16; C07K 17/00
(52) U.S. Cl. ................ 514/2; 514/12; 530/380
(58) Field of Search .................. 514/2, 12; 530/380

(56) References Cited

U.S. PATENT DOCUMENTS 5,236,904 A  8/1993 Gerstenberg et al. ......... 514/12

FOREIGN PATENT DOCUMENTS

| EP | 1223957 | 7/2002 |
|---|---|---|
| WO | WO9956785 | 11/1999 |
| WO | WO9960630 | 11/1999 |
| WO | WO 01/24809 A1 * | 9/2000 |

OTHER PUBLICATIONS

C Amant et al., Review Article, "Angiogenesis and Gene Therapy in Man," Drugs 1999, 58 Spec.Issue 1:33–36.*

Anthony, FW, et al. (1994) "Short Report: Identification of a specific pattern of vascular endothelial growth factor mRNA expression in human placenta and cultured placental fribroblasts," *Placenta* 15(5): 557–561 (Exhibit 1).

Breier G, et al. (1992) "Expression of vascular endothelial growth factor during enbryonic angiogenesis and endothelial cell differentation," *Development* 114(2): 521–532 (Exhibit 2).

Charnock–Jones, et al. (1993) "Identification and localization of alternately spliced mRNAs for vascular endothelial growth factor in human uterus and estrogen regulation in endometrial growth carcinoma cell lines," *Biology Reproduction* 48(5):1120–1128 (Exhibit 3).

De Jong JS, et al. (1998) "Expression of growth factors, growth–inhibiting factors, and their receptors in invasive breast cancer II: Correlation with proliferation and angiogenesis," *Journal Pathology* 184(1):53–57 (Exhibit 4).

Harada K., et al. (1996) "Vascular endothelial growth factor administration in chronic myocardial ischemia," *American Journal Physiology* 270 (No. 5, Part 2): 879–886 (Exhibit 5).

Isner JM., et al. (1995) "Arterial gene therapy for therapeutic angiogenesis in patients with peripheral artery disease," *Circulation* 91(11):2687–2692 (Exhibit 6).

Joukov, V., et al. (1996) "A novel vascular endothelial growth factor, VEGF–C, is a ligand for the Flt4 (VEGFR–3) and KDR (VEGFR–2) receptor tyrosine kinases," *EMBO Journal* 15(7): 1751 (Exhibit 7).

Neufeld G., et al (1994) "Vascular Endothelial Growth Factor and Its Receptors," *Progress Growth Factor Research* 5(1): 89–97 (Exhibit 9).

Olofsson, B., et al (1996) "Vascular endothelial growth factor B, a novel growth factor for endothelial cells," *Proceedings National Academy Science USA* 93(6): 2576–2581 (Exhibit 10).

Relf, M., et al. (1997) "Expression of the angiogenic factors vascular endothelial cell growth factor, acidic and basic fibroblast growth factor, tumor growth factor β–1, platelet–derived endothelial cell growth factor, placenta growth factor, and pleiotrophin in human primary breast cancer and its relation to angiogenesis," *Cancer Research* 57(5): 963–969 (Exhibit 11).

Soker S., et al. (1998) "Neuropilin–1 is expressed by endothelial and tumor cells as an isoformspecific receptor for vascular endothelial growth factor," *Cell* 92(6): 735–745 (Exhibit 12).

(List continued on next page.)

Primary Examiner—Ram Shukla
(74) Attorney, Agent, or Firm—John P. White; Cooper & Dunham LLP (57) ABSTRACT

This invention provides a method of increasing or maintaining the blood supply in the penis of a male subject which comprises administering to the subject an amount of vascular endothelial growth factor effective to increase or maintain the blood supply in the subject's penis. This invention provides a method of treating erectile dysfunction in a subject which comprises-administering to the subject an amount of vascular endothelial growth factor effective to increase the blood supply in the subject's penis and thereby treat the subject's erectile dysfunction. This invention provides a method of increasing or maintaining the blood supply in the penis of a subject which comprises introducing a nucleic acid comprising a gene encoding a vascular endothelial growth factor into a suitable cell under conditions such that the nucleic acid expresses vascular endothelial growth factor so as to thereby increase or maintain the blood supply in the subject's penis. This invention provides a method of increasing or maintaining the blood supply in the genital area of a female subject which comprises administering to the subject an amount of vascular endothelial growth factor effective to increase or maintain the blood supply in the subject's genital area.

5 Claims, 7 Drawing Sheets

OTHER PUBLICATIONS

Sugihara FW., et al. (1998) "A novel alternatively spliced form of murine vascular endothelial growth factor VEGF 115," *Journal Biological Chemistry* 273(5): 3033–3038 (Exhibit 13).

Takeshita S., er al. (1996) "Therapeutic angiogenesis following arterial gene transfer of vascular endothelial growth factor in a rabbit of hindlimb ischemia," *Biochemical & Biophysical Research Communications* 227(2): 628–635 (Exhibit 14).

Takeshita S., et al. (1994) "Therapeutic angiogenesis. A single intraaterial bolus of vascular endothelial growth factor, augments revascularization in a rabbit ischemic hindlimb model," *Journal Clinical Investigation* 93(2): 662–670 (Exhibit 15).

Terman, B.I., er al. (1996) "Biological properties of VEGF/VPF receptors," *Cancer Metastasis Review* 15(2): 159–163 (Exhibit 16).

Thomas, K.A., et al. (1996) "Vascular Endothelial Growth Factor, a potent and selective angiogenic agent," *Journal Biological Chemistry* 271(2): 603–606 (Exhibit 17).

Tischer, E., et al. (1991) "Human Gene for Vascular Endothelial Growth Factor," *Journal Biological Chemistry* 266(18): 11947–11957 (Exhibit 18).

Tsurumi, Y., et al. (1997) "Reciprocal relation between VEGF and NO in the regulation of endothelial integrity," *Nature Medicine* 3(8): 879–886 (Exhibit 19).

Cullinan–Bove, Kathleen et al. "Vascular endothelial growth factor/vascular permeability factor expression in the rat uterus: Rapid stimulation by estrogen correlates with estrogen–induced increases in uterine capillary permeability and growth." Endocrinology, vol. 133, No. 2, 1993, pp. 829–837.

Charnock–Jones, D.S. et al. "Identification and localization of alternately spliced mRNAs for vascular endothelial growth factor in human uterus and estrogen regulation in endometrial carcinoma cell lines." Biology of Reproduction, Society For The Study Of Reproduction, vol. 48. No. 5, 1993.

Burchardt M. et al. "Expression of messenger ribonucleic acid splice variants for vascular endothelial growth factor in the penis of adult rats and humans." Biology of Reproduction, vol. 60, No. 2, 1999.

Tarcan T. el al. "Age–related erectile and avoiding dysfunction: the role of arterial insufficiency." British Journal Of Urology, vol. 82, Suppl. 1, 1998.

Burchardt et al. "Vascular Endothelial Growth Factor A 110 (Fragment)." Database Treemblrel, AC#088911, 1999.

Te A.E. et al. "Neurotrophic factors in the rat penis." Journal Of Urology, vol. 152, No. 6, 1994.

Heaton J.P.W. et al. "A Therapeutic taxonomy of treatments for erectile dysfunction: an evolutionary imperative." International Journal of Impotence Research, vol. 9, No. 3, 1997.

Shabsigh A. et al. "The microvascular architecture of the rat vagina revealed by image analysis of vascular corrosion casts." International Journal of Impotence Research, vol. 11, Suppl. 1, 1999.

Truss, C.M. et al., (1997) "Intracavernous pharmacotherapy" World Journal of Urology, 15:71–77.

Neufeld G., et al (1996) "Similarities and differences between the vascular endothelial growth factor (VEGF).splice variants,"*Cancer & Metastasis Review* 15(2): 153–158 (Exhibit 8)

* cited by examiner

| | | | |
|---|---|---|---|
| Probe 164 | Exon 1-5 | 7 | 8 |

| | | | |
|---|---|---|---|
| Probe 164+ | Exon 1-5 | | 8 |
| VEGF 120 | 342 bp | | 18 |

| | | | |
|---|---|---|---|
| Probe 164+ | Exon 1-5 | | 8 |
| VEGF 144 | 342 bp | | 18 |

| | | | |
|---|---|---|---|
| Probe 164+ | Exon 1-5 | 7 | 8 |
| VEGF 164 | 492 bp | | |

| | | | |
|---|---|---|---|
| Probe 164+ | Exon 1-5 | 7 | 8 |
| VEGF 188 | 342 bp | 150 | |

VEGF 205 (433 bp) →

SEQUENCE LISTING

<160> NUMBER OF SEQ ID NOS: 4

<210> SEQ ID NO 1
<211> LENGTH: 21

-continued

```
<212> TYPE: DNA
<213> ORGANISM: HUMAN

<400> SEQUENCE: 1
tgcacccatg gcagaaggag g                                              21

<210> SEQ ID NO 2
<211> LENGTH: 21
<212> TYPE: DNA
<213> ORGANISM: HUMAN

<400> SEQUENCE: 2
tcaccgcctc ggcttgtcac a                                              21

<210> SEQ ID NO 3
<211> LENGTH: 21
<212> TYPE: DNA
<213> ORGANISM: RAT

<400> SEQUENCE: 3
tgcacccacg acagaagggg a                                              21

<210> SEQ ID NO 4
<211> LENGTH: 22
<212> TYPE: DNA
<213> ORGANISM: RAT

<400> SEQUENCE: 4
tcaccgcctt ggcttgtcac at                                             22
```

USES OF VASCULAR ENDOTHELIAL GROWTH FACTOR IN THE TREATMENT OF ERECTILE DYSFUNCTION

Throughout this application, various publications are referenced by Arabic numerals. Full citations for these publications may be found at the end of the specification immediately preceding the claims. The disclosure of these publications is hereby incorporated by reference into this application to describe more fully the art to which this invention pertains.

BACKGROUND OF THE INVENTION

Mammalian reproduction requires a physiological stimulation of male erectile tissues in the penis to mechanistically support the transfer of sperm from the male to the female. obviously then, defects that prevent an appropriate erectile tissue response can drastically interfere with reproductive capability. In humans, erectile dysfunction is considered to be a disease state and is referred to as the condition of "impotence". This condition impacts on the quality of life both of the male patients, as well as their wives/partners (1).

Erection is a hemodynamic phenomenon involving the tissue of the corpora cavernosa as well as the corpus spongiosum in the penis. This tissue is a complex admixture of smooth muscle, endothelial cells, fibroblasts and nerves interacting under stimulatory conditions to drastically enhance and maintain an accessory blood supply that imparts rigidity to the penis. Given the need for stringent control of blood flow during this response, it is no surprise that vascular insufficiency has the ability to drastically suppress erectile capability. In fact, penile vascular insufficiency is believed to be a very common pathomechanism of erectile dysfunction (2). This is associated with substantial pathologic changes in the erectile tissue leading to reduction in vascular smooth muscle cells and increases in collagen and fibrosis (3–6).

The currently available treatments of erectile dysfunction induce temporary erections at the same time of administration of such treatments. However, these treatments do no address or cure the basic vascular/cavernosal pathology causing erectile dysfunction. The rationale for a curative treatment that improves or repairs the vascular structure and function of the erectile tissue is based upon the understanding of erectile physiology and the pathophysiology of vascular erectile dysfunction. Consequently, it is prudent to pursue investigation of factors,hat induce new vascular structure formation or vasculogenesis. Several naturally occurring growth factors have been found to induce vasculogenesis (7–10). Such growth factors include the vascular endothelial growth factor (VEGF) family (11), the fibroblast growth factor (FGF) family (12, 13), transforming growth factor -alpha and -beta (TGF) (14), and platelet derived growth factor (PDGF) (15–17). Vascular endothelial growth factor (VEGF) may well be one of the most potent and interesting of these vascular growth factors. It is thought to play a role in embryonic vasculogenesis (18), maintenance of vascular structures in the adult and formation of new blood vessels in the adult in responses to ischemia and other pathologic states. Therapies that increase tissue levels of VEGF in laboratory animals or humans with peripheral vascular disease have resulted in a measurable increase in tissue vascularity (19–24).

In order to contemplate the potential of VEGF therapy for erectile dysfunction, a characterization was wanted of the extent to which VEGF is expressed in the mammalian penis and in erectile tissue, as well as a determination of which of the known isoforms of VEGF (derived from mRNA splice site variation) are most abundantly present in this tissue compared to other mammalian tissues. Here a survey of VEGF isoform expression (mRNA) in mature rat penis and in human erectile tissue is presented.

VEGF is a growth factor that acts preferentially on endothelial cells(18) . With the current focus of biomedical research on angiogenesis, the biology of VEGF has been under intense scrutiny. In humans, there are several different genes that encode VEGF-like proteins (49,50) , the most studied of these genes is that for VEGF-A (51, 52, 53). As described by several different laboratories, the VEGF-A gene gives rise to several different mature mRNA transcripts that differ in the protein products they encode (33, 34). These variant transcripts arise through an alternative splicing mechanism (30, 31, 54) and the abundance of any particular VEGF-A transcript differs, depending on the tissue examined (28). The most predominant VEGF-A transcripts found in adult tissues encode proteins of 188/189, 164/165 and 120/121 amino acids (rat/human) (28, 35). Other, rarer variant transcripts arising from VEGF-A have also been reported (encoding 205/206 and 144/145 amino acid proteins), but these forms were only found in a few tissues, mainly fetal in origin (VEGF 205/206: human fetal liver (32), sheep (41) and human placenta (42)/VEGF 144/145: human uterus (39), human endometrial carcinoma cells (39), sheep (41) and human placenta (42), respectively). During a preliminary survey of adult penile tissues for the expression of VEGF-A isoforms, it was found that the expression of VEGF-A mRNA splice variants encoding the 205/206 and 144/145 forms of VEGF can be identified by standard RT-PCR techniques and confirmed by cloning and sequencing from other adult rat and human tissues and cultured cells. These results suggest that these rarer splice variants of VEGF-A might have a wider tissue distribution than originally anticipated.

SUMMARY OF THE INVENTION

This invention provides a method of increasing or maintaining the blood supply in the penis of a male subject which comprises administering to the subject an amount of vascular endothelial growth factor effective to increase or maintain the blood supply in the subject's penis.

This invention provides a method of treating erectile dysfunction in a subject which comprises administering to the subject an amount of vascular endothelial growth factor effective to increase the blood supply in the subject's penis and thereby treat the subject's erectile dysfunction.

This invention provides a method of increasing or maintaining the density of vascular structures in the penis of a male subject which comprises administering to the subject an amount of vascular endothelial growth factor effective to increase or maintain the blood supply in the subject's penis.

This invention provides the above methods, wherein the vascular endothelial growth factor is VEGF-A 205/206, VEGF-A 188/189, VEGF-A 164/165, VEGF-A 144/145, VEGF-A 120/121, or VEGF-A 110.

This invention provides the above methods, wherein the vascular endothelial growth factor is administered intravenously, topically, transdermally, orally or by injection.

This invention provides the above methods, wherein the vascular endothelial growth factor is injected into the penis.

This invention provides the above methods, wherein the vascular endothelial growth factor is injected into corpora cavernosa or corpus spongiosum tissue.

This invention provides a method of increasing or maintaining the blood supply in the penis of a subject which comprises introducing a nucleic acid comprising a gene encoding a vascular endothelial growth factor into a suitable cell under conditions such that the nucleic acid expresses vascular endothelial growth factor so as to thereby increase or maintain the blood supply in the subject's penis.

This invention provides a method of increasing or maintaining the blood supply in the genital area of a female subject which comprises administering to the subject an amount of vascular endothelial growth factor effective to increase or maintain the blood supply in the subject's genital area.

BRIEF DESCRIPTION OF THE FIGURES

FIG. 1

Diagram Characterizing Some Major VEGF-A cDNA Splice Variants Isoforms That Were Previously Detected in Rat Tissues and Were Also Observed in the Study:

The mammalian VEGF gene is split into eight exons (represented by boxes). Alternative splicing of these exons give rise to six molecular forms previously detected in rat tissues (VEGF 205 amino acids—120 amino acids) as well as a form (VEGF 110 amino acids) that was discovered by our screening and sequencing of VEGF cDNA clones from the rat penis. The nucleotide length of the exon boxes is described above the VEGF 205 form and below the VEGF 110 form.

FIG. 2

RT-PCR Characterization of VEGF-A cDNA Splice Variants Expressed in Rat and Human Tissues:

(A) Agarose gel profile of products resulting from RT-PCR amplification of VEGF-A mRNA splice variants present in rat tissues. Both rat lung and penis show presence of cDNA products characteristic of amplification of VEGF-A splice forms 188, 164, 144 and 120. These cDNA amplification products migrate equivalently with the characterized VEGF isoform markers present individually in the lanes on the right as marked. Whereas 188 form appears to more predominant in lung, the 164 form appears to be most abundant in penis. M.W.=lanes containing molecular weight markers.

(B) Agarose gel profile of products resulting from RT-PCR amplification of VEGF-A mRNA splice variants present in human cells and tissue. Both the LNCaP cell line RNA and human cavernosal RNA allow the amplification of 4 major splice variants of VEGF A (189, 165, 145 and 121). As with the results from amplification of rat penis RNA (4th lane), the 165 AA splice variant is more abundant in human penis than the 189 splice variant. Similarly amplified products from rat tissues (penis and lung) are compared on right lanes. M.W.=Lane containing molecular weight marker. Molecular sizes of amplified fragments are shown on the right.

FIG. 3

Rnase Protection Assays of RNAs Extracted From Rat Lung or Penis to Measure Relative Abundance of VEGF-A mRNA Splice Variant Expression:

(A) RNase protection assay using 32P-labeled large (VEGF 188) antisense riboprobe. Autoradiograph of gel containing RNase digestion products reveals the presence of a protected 564 bp fragment characterizing abundant expression of VEGF 188 splice variant only in rat lung, not in rat penis mRNA.

(B) RNase protection assay using 32P-labeled small (VEGF 164) antisense riboprobe. Autoradiograph of gel containing RNase digestion products reveals the presence of abundant 150 bp protected fragment in lung, not penis RNA, confirming abundant expression of 188 splice variant in this site. Likewise the presence of a 492 bp protected fragment in both rat lung and penis RNA characterizes expression of the VEGF 164 splice isoform in both tissues. Finally, the presence of 342 bp protected fragment in penis RNA, while potentially resulting from hybridization with the 188 or 144 splice forms, is most likely to result from the digestion of an abundant VEGF 120 splice isoform in the penis based on our inability to detect protection of the other specific fragments that would result from hybridization of the large (VEGF 188) probe with the 188 or 144 splice variants. Diagrams (at lower part of figures) identify the size of potential protected fragments that could result using the larger probe (A) or the smaller VEGF probe (B). Sizes of molecular weight markers (M.W.) are indicated to the right, sizes of specifically designated protected fragments are indicated to the left. Control lanes include yeast RNA hybridized to probe +digestion or yeast RNA hybridized to probe −digestion.

FIG. 4

RT-PCR Amplification Demonstrates VEGF Splice Isoform (144/145) Expression in Rat and Human Tissues and Cells:

PCR primers within exon 1 and 8 of VEGF-A were used to amplify cDNA from rat lung and penis or from human penis or LNCaP cell lines. Agarose gel of reaction products stained with ethidium bromide. Arrows show position of bands at 360/363 bp (VEGF 120/121), 432/435 bp (VEGF 144/145), 492/495 bp (VEGF 164/165) and 564/567 bp (VEGF 188/189). Right side of gel contains a representative ladder generated by PCR-amplification of individual clones containing the referenced VEGF cDNA fragment or a molecular weight marker (M.W.)

FIG. 5

RT-PCR Amplification Demonstrates VEGF Splice Isoform (VEGF 205) Expression in Rat Tissues:

PCR primers within exon 1 and 6B of VEGF-A were used to amplify cDNA from adult rat lung and penis. Agarose gel of reaction products stained with ethidium bromide. Arrow show position of bands at 433bp (VEGF 205). Right lanes contain RT-PCR reaction products using exon ⅛ primers on rat tissues or cloned plasmids containing defined splice variant cDNA for VEGF-A as indicated. M.W. is a molecular weight marker.

DETAILED DESCRIPTION OF THE INVENTION

This invention provides a method of increasing or maintaining the blood supply in the penis of a male subject which comprises administering to the subject an amount of vascular endothelial growth factor effective to increase or maintain the blood supply in the subject's penis.

As used herein, "increasing" means that the blood supply is at a level that is higher than that which would exist in a control experiment without using said method.

As used herein, "maintaining" means that the blood supply is kept at a level which is greater than or equal to the blood supply that exists in a control situation without using said method.

As used herein, "subject" includes any animal or artificially modified animal. This includes but is not limited to animals such as mice, rats, dogs, guinea pigs, ferrets, rabbits, primates, equine, bovine, avian, caprine, canine, feline. As used herein, "subject" also includes a human. In the preferred embodiment, the subject is human.

This invention provides a method of treating erectile dysfunction in a subject which comprises administering to the subject an amount of vascular endothelial growth factor effective to increase the blood supply in the subject's penis and thereby treat the subject's erectile dysfunction.

As used herein, "treating" means either slowing, stopping or reversing erectile dysfunction. In the preferred embodiment, treating means reversing to the point of eliminating erectile dysfunction.

This invention provides a method of increasing or maintaining the density of vascular structures in the penis of a male subject which comprises administering to the subject an amount of vascular endothelial growth factor effective to increase or maintain the blood supply in the subject's penis.

This invention provides the above methods, wherein the vascular endothelial growth factor is VEGF-A 205/206, VEGF-A 188/189, VEGF-A 164/165, VEGF-A 144/145, VEGF-A 120/121, or VEGF-A 110.

As used herein, "VEGF-A 205/206" refers to the VEGF-A rat 205 amino acid splice variant or VEGF-A human 206 amino acid splice variant.

As used herein, "VEGF-A 188/18911" refers to the VEGF-A rat 188 amino acid splice variant or VEGF-A human 189 amino acid splice variant.

As used herein, "VEGF-A 164/165" refers to the VEGF-A rat 164 amino acid splice variant or VEGF-A human. 165 amino acid splice variant.

As used herein, "VEGF-A 144/145" refers to the VEGF-A rat 144 amino acid splice variant or VEGF-A human 145 amino acid splice variant.

As used herein, "VEGF-A 120/121" refers to the VEGF-A rat 120 amino acid splice variant or VEGF-A human 121 amino acid splice variant.

As used herein, "VEGF-A 110" refers to the VEGF-A human 110 amino acid splice variant.

This invention provides the above methods, wherein the vascular endothelial growth factor is administered intravenously, topically, transdermally, orally or by injection.

This invention provides the above methods, wherein the vascular endothelial growth factor is injected into the penis.

This invention provides the above methods, wherein the vascular endothelial growth factor is injected into corpora cavernosa tissue.

This invention provides the above methods, wherein the vascular endothelial growth factor is injected into corpus spongiosum tissue.

This invention provides a method of increasing or maintaining the blood supply in the penis of a subject which comprises introducing a nucleic acid comprising a gene encoding a vascular endothelial growth factor into a suitable cell under conditions such that the nucleic acid expresses vascular endothelial growth factor so as to thereby increase or maintain the blood supply in the subject's penis.

As used herein, the term "nucleic acid," refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

As used herein, "suitable" means a cell which can express the vascular endothelial growth factor gene such that it produces vascular endothelial growth factor to thereby increase or maintain the blood supply in the subject's penis.

The term "vector", refers to viral expression systems, autonomous self-replicating circular DNA (plasmids), and includes both expression and nonexpression plasmids. Where a recombinant microorganism or cell culture is described as hosting an "expression vector, " this includes both extrachromosomal circular DNA and DNA that has been incorporated into the host chromosome(s) . Where a vector is being maintained by a host cell, the vector may either be stably replicated by the cells during mitosis as an autonomous structure, or is incorporated within the host's genome.

This invention provides the above method, wherein the nucleic acid comprises a vector.

As used herein, "vector" includes viral expression systems, autonomous self-replicating circular DNA plasmids and includes both expression and nonexpression plasmids.

This invention provides a method of increasing or maintaining the density of vascular structures in the penis of a subject which comprises introducing a nucleic acid comprising a gene encoding a vascular endothelial growth factor into a suitable cell under conditions such that the nucleic acid expresses vascular endothelial growth factor so as to thereby increase or maintain the blood supply in the subject's penis.

This invention provides a method of increasing or maintaining the blood supply in the genital area of a female subject which comprises administering to the subject an amount of vascular endothelial growth factor effective to increase or maintain the blood supply in the subject's genital area.

This invention provides a method of increasing or maintaining the density of vascular structures in the genital area of a female subject which comprises administering to the subject an amount of vascular endothelial growth factor effective to increase or maintain the blood supply in the subject's genital area.

This invention will be better understood from the Experimental Details which follow. However, one skilled in the art will readily appreciate that the specific methods and results discussed are merely illustrative of the invention as described more fully in the claims which follow thereafter.

Experimental Details

A. Materials and Methods

1. Human Tissues

Specimens of cavernosal tissue of (12) humans (ages 39–79) were surgically removed from the penoscrotal junction at the time of penile prosthesis implantation under an IRB-approved protocol. These biopsies measured approximately 5×5×10 mm. The specimens were immediately frozen under liquid nitrogen and were stored at −70° C. until processing.

2. Laboratory Animals and Tissues

Age-matched male Sprague Dawley rats (8 weeks, Camm Laboratories, Camden, N.J.), were obtained under an IACUC approved protocol and were maintained on a 12 hour daylight cycle with food and water available ad libitum. Rats were sacrificed by a lethal overdose of sodium pentobarbital. Lung and penis were harvested immediately. Penile tissue was obtained through a circular incision made at the corona with subsequent removal of the foreskin and the shaft skin and amputation of the penis. The glans, which contains a significant amount of skin, was also removed. Excess blood was removed by gently blotting the penis on sterile cotton gauze and the specimen was flash frozen in liquid nitrogen and stored at −70° C. until use. This procedure provided cryopreserved, deskinned penile shafts that contained mostly erectile tissue.

3. RNA Extraction

Tissue (pooled penis from 20 rats or pooled 12 human specimens) was first pulverized under liquid nitrogen to a fine powder. Total RNA was isolated from the tissue powder using an RNAzol (Tel-Test, Inc., Friendswoods, Tex.) extraction procedure following the manufacturers protocol [25, 26]. RNA concentration was determined by spectrophotometry at 260 nm, and to ensure the RNA was not degraded, each sample was analyzed by electrophoresis on a 1% denaturing formaldehyde gel. Total RNA was extracted from the prostate carcinoma cell line, LNCaP, using a modification of this procedure [27].

4. RT-PCR to Amplify VEGF cDNAs

1ug total RNA was used for first-strand cDNA synthesis. The RNA was annealed to 0.5 ug oligo(dT) primer (Gibco BRL, Grand Island, N.Y.) in a volume of 20 ul at 70° C. for 10 min. then chilled on ice quickly for 2 min. 10 mM dNTPs, 5×Ist strand buffer, 0, 1 M dithiothreitol (DTT), 10 U RNase Inhibitor (Gibco BRL), and 200 U Supersript II reverse transcriptase (Gibco BRL) in a final volume of 50 ul were added. The reaction mix was incubated by heating 37° C. for 90 min, and the cDNA was stored at −20° C. until used.

Polymerase chain reaction (PCR) techniques were then used to identify the presence of VEGF isoforms in the RNA samples. Primers used for the amplification assay were slight modifications of those published previously [28]. Because these primers initiate within the first exon and terminate within the eighth exon of VEGF-A, they enable amplification of all the known VEGF splice variants. The oligonucleotide sequences of the primers used are as follow:

| Primer | 5' |
| --- | --- |
| Species | human |
| Location | start of exon 1 |
| Nucleotide sequence | 5' TGC ACC CAT GGC AGA AGG AGG 3' (SEQ ID NO: 1) |
| Primer | 3' |
| Species | human |
| Location | end of exon 8 |
| Nucleotide sequence | 5' TCA CCG CCT CGG CTT GTC ACA 3' (SEQ ID NO: 2) |
| Primer | 5' |
| Species | rat |
| Location | start of exon 1 |
| Nucleotide sequence | 5' TGC ACC CAC GAC AGA AGG GGA 3' (SEQ ID NO: 3) |
| Primer | 3' |
| Species | rat |
| Location | end of exon 8 |
| Nucleotide sequence | 5' TCA CCG CCT TGG CTT GTC ACA T 3' (SEQ ID NO: 4) |

The PCR reaction mix contained 10× reaction buffer (100 mM Tris, 500 mM KCL, 1.5 mM MgCl 2, pH 8.3), d NTP Mix (10 mM each DATP, dGTP, dCTP and dTTP at neutral pH), 100 pmol upstream primer (5'- human/5'- rat), 100 pmol downstream primer (3'-human/3'-rat), 2.5 U Taq DNA polymerase (Boehringer Mannheim Biochemicals, Indianapolis, Ind.), 10 ul cDNA, and sterile water to 50 ul. PCR was carried out using a DNA Thermal Cycler (Perkin Elmer Cetus, Norwalk, Conn.) as follows: 94° C. for 7 min.; then 35 cycles of denaturation at 94° C. for 1 min., annealing and extension at 72° C. for 1 min. each. The PCR products (20 ul of lung-rat-/LNCaP- and 35 ul of penis-rat-/penis-human-reaction mix) were analyzed by electrophoresis on a 2% agarose gel that was subsequently stained with ethidium bromide for visualization of DNA bands. A 100 base pair ladder DNA molecular weight marker was used (Boehringer Mannheim Biochemicals) to provide a size reference for the test reactions.

5. Cloning and Sequencing of RT-PCR Products 1 ul of penis-rat-PCR products were ligated into the pGEM-T easy Vector DNA and were used to transform DH5-(competent cells. Transformants containing cDNA inserts were characterized for insert size by analysis of Eco RI digested minipreps. A variety of plasmid vectors containing cDNA inserts of different sizes were then sequenced from the double-stranded templates by standard dideoxynucleotide sequencing techniques. These sequences were compared to the human or rat VEGF cDNA sequences present in genbank to identify exon structure.

6. RNase Protection Assay for VEGF mRNA Isoforms

Two antisense RNA probes for VEGF cDNA were used. One was in vitro transcribed from an Apa I-digested vector containing the rat VEGF 164 splice isoform cDNA whereas the other was in vitro transcribed from an Apa I-digested vector containing the rat VEGF 188 splice isoform DNA using SP6-polymerase. The in vitro transcription reactions were carried out in the presence of 250 uCi [$^{32}$P]-UTP (NEN Life Science Products, Boston, Mass.) using the reagents provided in an in vitro-transcription kit (MAXIscript, Ambion, Inc., Austin, Tex.) according to the manufacturer's instructions. Individual labeled antisense probes (619 bases for the VEGF 164 probe and 691 bases for the VEGF 188 probe) were purified by electrophoresis on a denaturing 5% acrylamide gel and were then eluted from the gel into elution buffer (from RPA II kit, Ambion, Inc.). These probes were used in solution hybridization procedures with 20 ug of rat lung RNA or 30 ug of penis RNA using the manufacturer's recommendations provided in the RNase assay kit (RPA II, Ambion, Inc.) overnight. Hybridized specimens were digested with a nuclease cocktail provided in the RPA II kit and the digests were subsequently analyzed by electrophoresis on 5% acrylamide sequencing gels adjacent to molecular weight marker lanes.

Some control reactions included labeled probes hybridized with yeast RNA (20 ug) (with/without RNase digestion). Gels were exposed to Kodak XAR-5 film to produce an autoradiograph showing the presence of RNase-protected bands.

B. Results and Discussion

Erectile dysfunction is often associated with problems in vascular perfusion to the erectile components of the penis. In order to better understand the factors that control vascular formation and perfusion in the erectile tissues of the penis, we have begun to characterize the expression of vascular endothelial growth factor (VEGF) in penis tissues. VEGF is one of several polypeptides that has significant angiogenic activity in vitro and in vivo. Extensive characterization of the VEGF gene and its products has shown that several different mature mRNA transcripts exist, originating from alternative splicing of the basic VEGF transcript. These variant transcripts can encode peptides with different biological activities.

Penile tissue was obtained from adult rats and from human patients undergoing penile prosthesis implantation. Analysis of the forms of VEGF transcripts was performed using a reverse transcriptase-polymerase chain reaction (RT-PCR) technique with primer pairs derived from the first and eight exon of the VEGF gene. The expression levels of the various isoforms in the rat penis were then quantified using RNase Protection Assays. Four previously described splice variants of VEGF mRNA (VEGF 120, 144, 164, 188) were detected in rat and human penile tissues. In contrast to rat lung where the most abundant form of VEGF MRNA is the 188 splice isoform, VEGF 164 is the most abundant transcript detected in the penis. Finally, sequence analysis of numerous VEGF cDNA clones obtained from rat penis demonstrated the presence of a previously undescribed VEGF splice variant that could give rise to a protein of 110 amino acid residues (VEGF 110, GenBank accession number AF080594[3]). In summary, a number of VEGF mRNA isoforms are expressed in the rat and human penis with the splice variant encoding a 164 amino acid protein present in greatest abundance. This study is a prelude for attempts to genetically manipulate VEGF expression in the penis as a therapy for erectile dysfunction.

Figure 1:
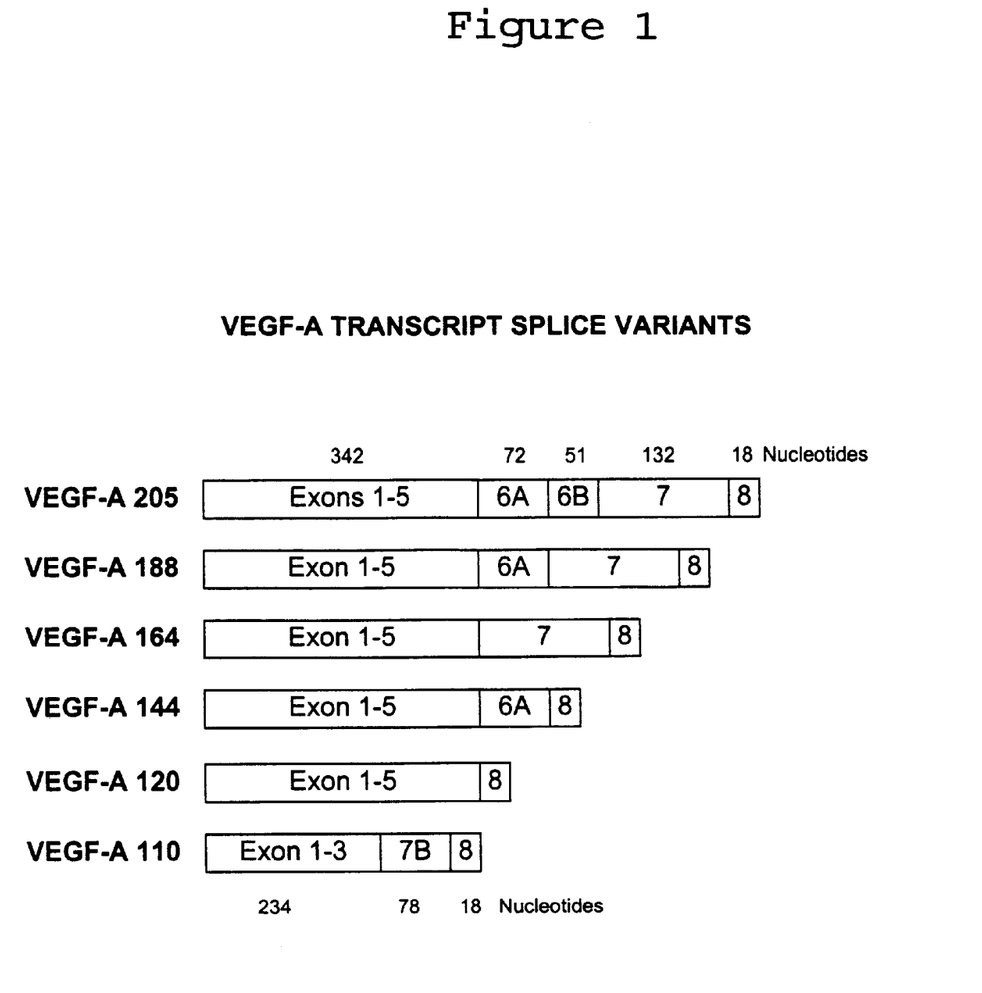

1. RT-PCR Analysis of VEGF mRNA Splice Variant Expression in Rat and Human Penis The mammalian VEGF gene [29] is known to consist of at least 8 exons that can be assembled, through alternative splicing [30–32], into a number of variant mRNA molecules that have the potential to encode differing proteins, each having mitogenic activity for the endothelial cell [33, 34]. Both human and rodent cell lines and tissues have been characterized for the expression of these VEGF splice variants and the prominent forms found in adult tissues include transcripts that can encode for 121, 165 or 189 amino acid (AA) containing proteins (in humans) [35–38]. Other VEGF splice variants have been detected in much lower abundance, for example, a 145 AA- encoding transcript for VEGF has been found in human uterine and placental tissue [39–41] as well as a 206 AA -encoding transcript that was found in fetal liver and placenta [41, 42]. Of this group of VEGF splice variants, all transcripts contain the first five VEGF exons as well as the last (eighth) exon but differ in the inclusion and/or arrangement of the sixth and seventh exon. Virtually identical VEGF splice variants have also been described in rodent tissues, however the variant rodent VEGF transcripts generally encode for a protein product containing one amino acid less than the human counterpart (see FIG. 1) [28, 43].

Figure 2A:
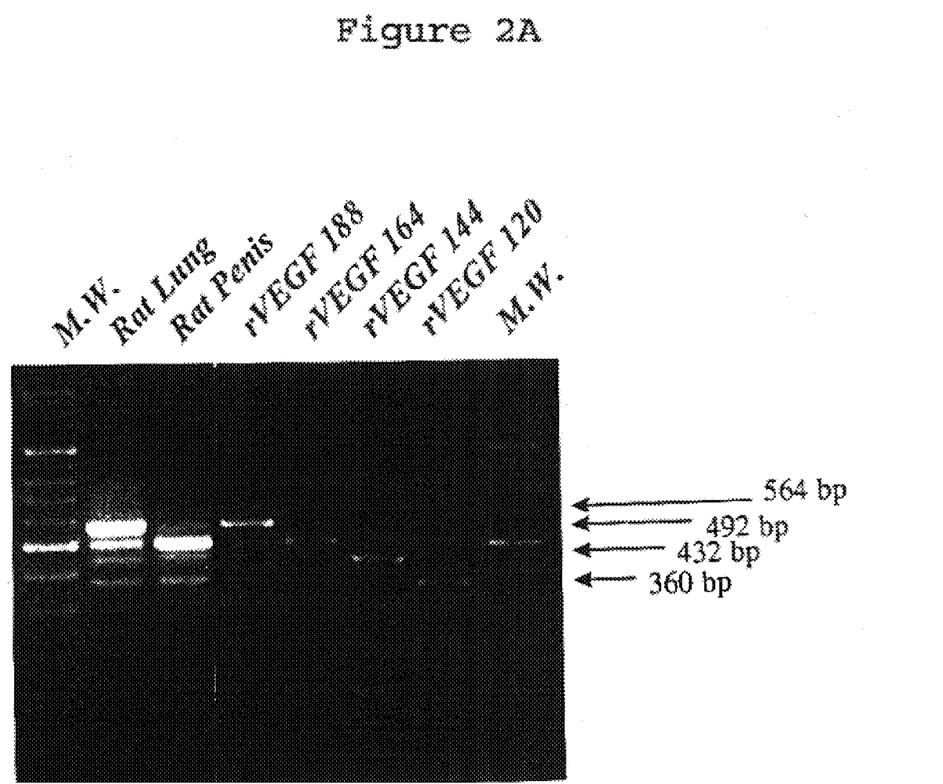

Using a RT-PCR screening method, we attempted to identify the VEGF mRNA splice variants that are expressed in rat and human penile tissues. Oligonucleotide primers designed to amplify cDNA from the first to the eighth exon of rat VEGF were used in a PCR amplification reaction of cDNA made from RNA extracted from rat lung or from rat penis. The RT-PCR amplification products were examined by electrophoresis on an agarose gel followed by ethidium bromide staining. As expected (FIG. 2A), these primers amplified three distinct cDNA fragments of 564, 492 and 360 bp in size from the rat lung cDNA (corresponding to the expected 188, 164 and 120 rat VEGF AA-encoding isoforms) as well as a distinct cDNA fragment of 432 bp. All of these cDNA fragments were also amplified from the cDNA of rat penis. Although the RT-PCR screening method was not designed to be quantitative, there appeared to be a distinct difference in the abundance of these RT-PCR Products between rat lung and penis tissue. The most predominant of the VEGF cDNAs amplified from lung RNA encoded the 188 AA isoform of VEGF whereas the most predominant transcript amplified from penis RNA appeared to be the one encoding the 164 AA isoform of VEGF (FIG. 2A). Each of these cDNA fragments was individually cloned into plasmids so that they could be sequenced and confirmed as VEGF splice variants. The sequencing confirmed our identification of the 188, 164 and 120 AA forms as well as confirmed that the 432 bp amplification product was the VEGF transcript variant encoding the 144 AA form of VEGF that was previously found only in uterine and placental tissues. More surprisingly in our survey of the cDNA clones resulting from RT-PCR amplification, we found one cDNA clone (330 bp) containing a novel splice variant of VEGF A that has never before been described (see FIG. 1). This splice variant contained the entire first three exons of rat VEGF-A spliced to a partial exon 7 (now referred to as exon 7B) and was terminated by the entire exon 8. It is likely that the partial exon 7 included in this novel transcript (7B) was another of the many splice adoptions of the VEGF A transcript since a canonical splice donor sequence (CCGCAG/) [44] was present at the end of the region of exon 7A that was deleted from this particular splice variant. Although this splice variant must be present in much lower abundance than any of the better known forms, this novel VEGF A splice variant does have the potential to encode a 110 amino acids isoform of VEGF-A.

Figure 2B:
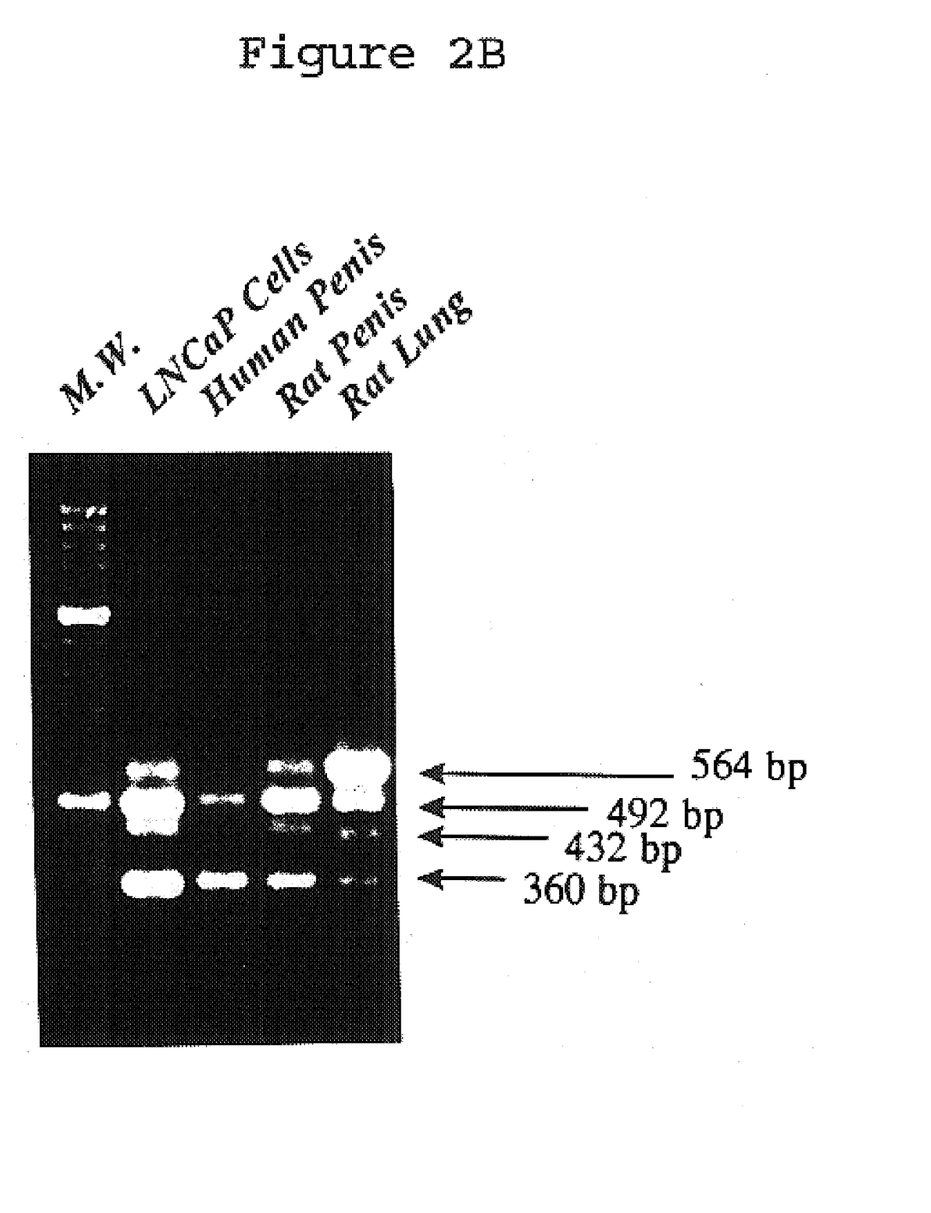

Similar primer sets were utilized to amplify cDNA that was reverse transcribed from human penis RNA and from RNA extracted from a human prostate cancer cell line, LNCaP, that is known to express VEGF-A in abundance. FIG. 2B shows the ethidium bromide stained agarose gel on which the amplification products from human penis cDNA, LNCaP cell cDNA or rat tissue (penis and lung) cDNA were electrophoresed. As can be seen from the results shown here, human penis (and human LNCaP cells) expresses the identical repertoire of VEGF splice variant isoforms that were found in the rat penis (including the 189, 165, 145 and 121 AA encoding isoforms). Moreover, these isoforms were present in similar abundance to the rat penis isoforms.

2. RNase Protection Assay to Confirm Relative Abundance of VEGF A Transcripts in Rat Penis In order to confirm and better quantify that the predominant VEGF-A transcript splice variants expressed in rat penis differed significantly in abundance from the forms expressed in rat lung, we developed an RNase protection assay that would allow us to distinguish the relative abundance of the different rat VEGF-A splice variants in RNA samples. $^{32}$P-radiolabeled probes for the 188 AA or the 164 AA splice variant of rat VEGF A cDNA were prepared by in vitro transcription of expression plasmids containing these respective cDNA inserts. The probes were individually hybridized to RNAs extracted from rat lung or rat penis and were then digested with a nuclease cocktail and electrophoresed on a polyacrylamide gel. The gel was exposed to film for autoradiography and the signal intensity of the protected fragments on this assay demonstrates the relative abundance of the corresponding transcript.

Figure 3A:
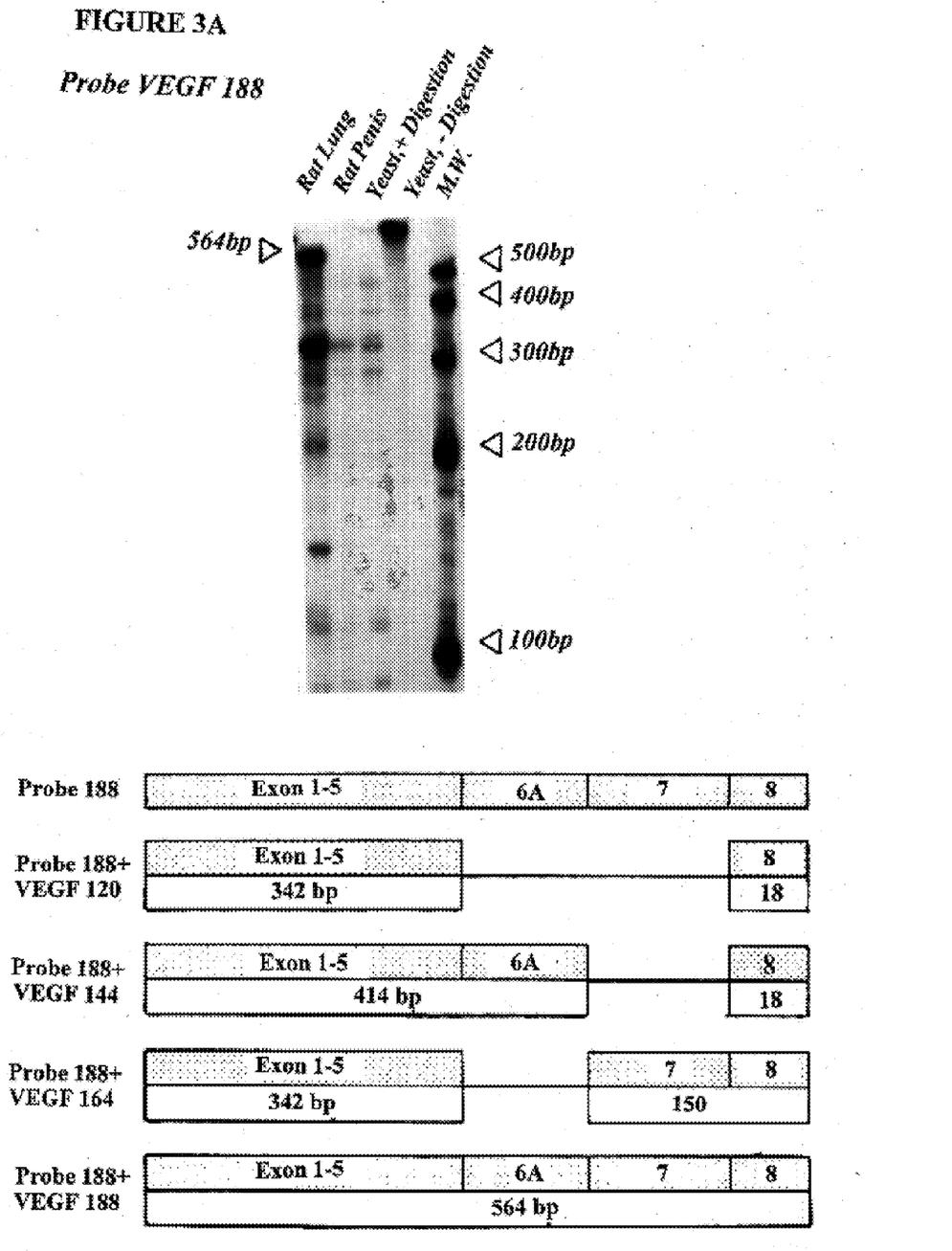
Figure 3B:
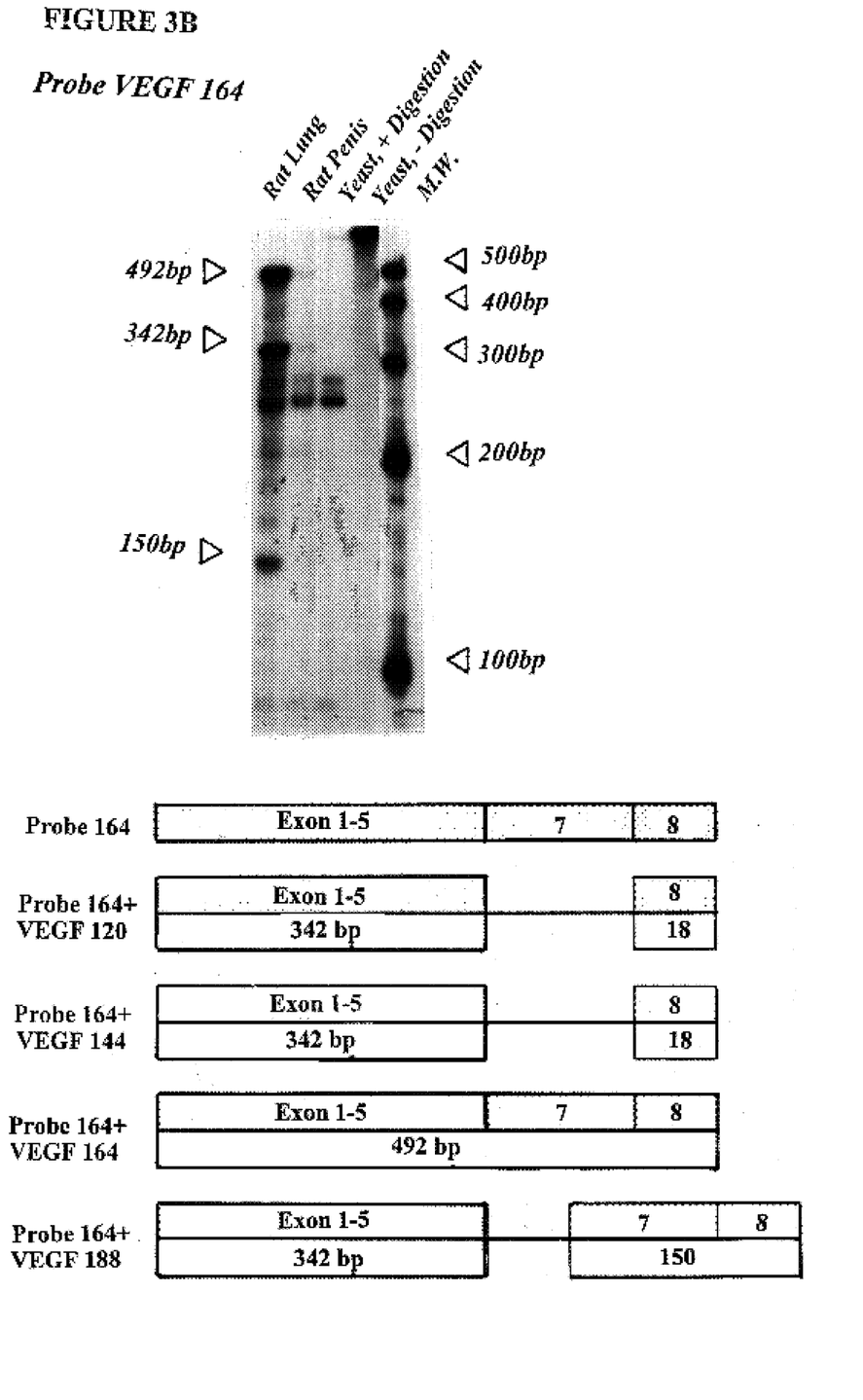

This two-probe assay was designed to demonstrate the presence of the VEGF isoforms through the detection of certain "diagnostic" fragments. For example, when using the larger transcript as a probe (the 188 splice isoform), the presence of a protected fragment at 564 bp would distinguish and confirm the presence of the 188 splice variant in the test mRNA specimen whereas the presence of a protected 150 bp fragment in the digest would distinguish the presence of the 164 splice variant (see Diagram at lower part of FIG. 3A). Likewise, when using the smaller transcript as a probe (164 splice isoform), the presence of a protected fragment of 492 bp would confirm the presence of the 164 splice variant in the test specimen (See Diagram at lower part of FIG. 3B).

The results (FIGS. 3A and 3B) of this RNase protection assay showed that, in rat lung, the most abundant splice variants of VEGF-A mRNA are for the 188 and the 164 isoforms, confirming the earlier experiment involving RT-PCR amplification of VEGF A isoforms (FIGS. 2A/2B)

as well as other reports [39]. In rat penis mRNA, we did not observe significant protection of a 564 bp fragment nor the 414 bp fragment using the larger splice isoform probe, indicating a much lower abundance of the 188 splice variant mRNA in penis mRNA compared to lung as well as a low abundance of the 144 splice variant in penis mRNA. With the smaller transcript as a probe, we were able to identify the presence of protected fragments at 492 bp and 342 bp, confirming the more abundant presence of the 164 and 120 isoform splice variants in penis mRNA. Again, this observation supports the RT-PCR experiments on rat penis in which we found that the 164 and 120 splice isoforms appeared to be the most abundant VEGF splice variants present in rat penis mRNA (FIG. 2A/2B).

3. Expression of VEGF Splice Variants 144/145 and 205/206 in Adult Male Tissues

Figure 4:
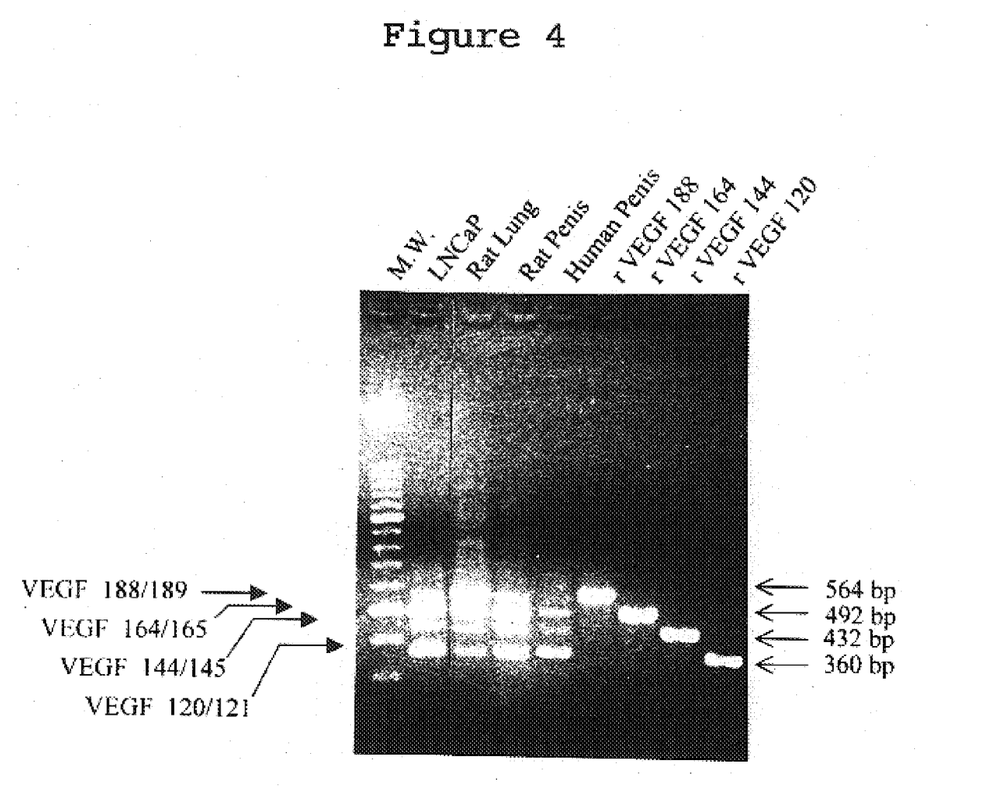

A standard RT-PCR technique was used to detect VEGF splice isoforms. Using an upstream primer starting in VEGF exon 1 and a downstream primer from VEGF exon 8, RT-PCR was performed on RNAs extracted from mature rat lung and penis as well as from a human prostate cancer cell line LNCaP. When the RT-PCR reaction products were analyzed by agarose gel electrophoresis, 4 major bands were detected from each of the reactions (FIG. 4). The size of 3 of these bands (at 360/363, 492/495 and 564/567 basepairs (rat/human)) would correspond to the expected transcript sizes encoding the 120/121, 164/165, and 188/189 AA isoforms of VEGF-A. However, an additional band at 432/435 bp, clearly visible in the reaction products from rat lung/penis and human penis/LNCaP cells, would more correspond with the expected size of the 144/145 splice form of VEGF-A (FIG. 4), previously only detected in placental and uterine tissues (sheep and humans) (41, 42, 39) and in cultured human endometrial carcinoma cells (39). The amplification products from these reactions were individually cloned into plasmid sequencing vectors and were sequenced. The sequences obtained confirmed our identification of the 120/121, 165/165, and 188/189 AA splice isoforms as well as the presence of the supposedly more rare 144/145 splice variant in the RNAa from these cells/tissues.

Figure 5:
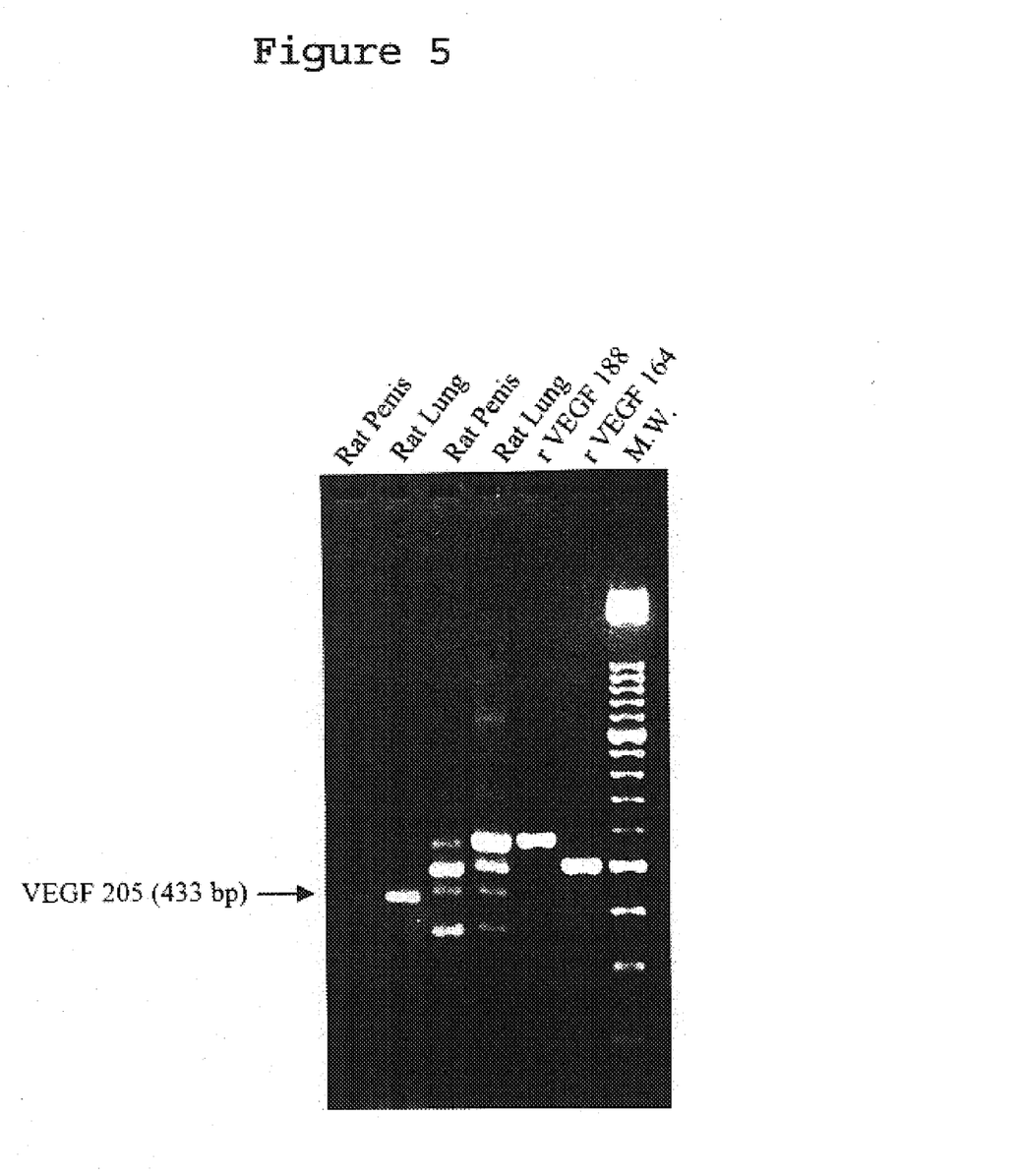

In the results of the previous RT-PCR reaction, we did not find the clear presence of a larger, 615 bp product, that would have resulted from the corresponding amplification of the VEGF-A splice isoform encoding a 205/206 AA peptide. However, the RT-PCR reaction was subsequently repeated using the same upstream primer (starting from exon 1) with a different downstream primer, (complimentary to the last five bases of exon 6A and continuing into the first 19 bases of exon 6B). The 6B exon of VEGF-A is found only in the VEGF 205/206 splice isoform, therefore this second primerpair was designed to selectively amplify the other supposedly rare isoform, VEGF 205. The application of this second primer pair showed a band at 433 basepairs in the amplification products from RNAs extracted from rat lung and penis (FIG. 5), a size that would be expected if the VEGF 205/206 splice isoform was present in the RNAs. The identity of this fragment was also confirmed, at least for the rat lung, by cloning and sequencing the 433 bp amplification product. This sequence showed complete homology to the rat VEGF-205 mRNA splice variant.

In conclusion, these results indicate that the rarer splice variants of VEGF-A (encoding the 144/145 and 205/206 AA forms) are probably more widely expressed in adult rat and human tissues than previously suspected. The PCR reaction conditions under which these rare splice variants of VEGF were detected were not so vigorous as to amplify such rare transcripts as those referred to as "basal" in nature. Although the transcript encoding the 144/145 splice variant was seemingly amplified less than the 120/121, 164/154, or 188/189 variants, it was well within detection limits of simple DNA staining techniques. However, the apparently lower abundance expression of VEGF 144/145 and 205/206 in these tissues (when compared to the more predominant VEGF splice variants) probably explains the failure of other investigators to identify their presence, especially in tissues that have been subject to repeated VEGF mRNA characterization, such as lung.

Experimental Discussion

Erectile function is dependent on the development of an appropriate penile vasculature and maintenance of an effective blood supply to the erectile tissues of the penis. The development and growth of a vascular system is referred to as angiogenesis and vasculogenesis. These processes are governed by several types of growth factors, including basic FGF (bFGF) and VEGF. Previously, we described the abundant presence of a heparin-binding growth factor in rat penis that had a functional activity that could be neutralized by antibodies to bFGF, suggesting that this substance was indeed bFGF [45]. Here we characterized the mRNA of rat and human penis to evaluate whether any of the many mRNA splice isoforms of VEGF are expressed in penile tissues and to determine which of the multiple splice isoforms might be the most abundantly expressed in the penis.

These results show that several different mRNA splice variants of VEGF-A mRNA are expressed in both rat and human penis and that there appears to be a distinct difference in the abundance of the different VEGF-A splice isoforms when compared to another rat tissue (rat lung) in which VEGF-A expression is known to be abundant. Whereas it has been confirmed that the rat lung expresses most abundantly an mRNA encoding the 188 splice variant, the rat penis, in contrast, expresses the 164 splice variant of VEGF-A mRNA at greatest abundance. Other VEGF splice variants, including the previously described 120 splice variant are also expressed at much lower levels by the lung and the penis. The ability to detect the presence of the 144 VEGF-A splice variant which was previously found only in placenta and some female reproductive tissues (uterus) was also surprising [39–42]. Moreover, the sequencing studies of a large number of VEGF cDNAs that were obtained following RT-PCR amplification of rat penis mRNA revealed the presence of a new splice variant of VEGF-A which has the more unusual characteristic of retaining the first 3 exons (instead of the first 5) as well as having an apparent splice within the $7^{th}$ exon. This splice variant is likely to be present in extremely low abundance, as we never detected a significant 330 bp amplification product in our RT-PCR experiments, nor was the corresponding protected exon fragments in our RNase protection experiments ever found. While the possibility was considered that this unusual splice variant of VEGF might not be able to produce an angiogenic peptide, it is of interest that another rare splice variant of (mouse) VEGF mRNA has also been described, containing only the first three exons of VEGF. This splice variant (VEGF 115) has been shown to encode a peptide that is able to bind to VEGF receptor and activate mitogenesis of endothelial cells [46]. Therefore, the unusual VEGF splice variant (VEGF 110) observed in these studies, although seemingly rare and low in abundance, probably has the potential to produce a functional VEGF peptide.

The recent approval by the FDA of Sildenafil citrate as the first oral therapy for erectile dysfunction has become a landmark for the development of pharmacotherapy for erectile dysfunction. However, all current pharmacologic treatments of erectile dysfunction consist of "on-demand" medications that produce temporary erections. At this time there is no curative treatment for erectile dysfunction. The work in this project is based on our conceptualization of the induction of vasculogenesis in the erectile tissue as a potential cure for the reduction of vascular elements frequently encountered in vasculogenic erectile dysfunction. In this descriptive study, VEGF-A mRNA expression was surveyed in rodent and human penis. The present characterization of the various VEGF isoforms in the erectile tissues is motivated by our interest in defining the angiogenic growth factors that regulate penile vasculogenesis and potentially exploiting these findings for therapeutic applications to treat human impotence. One could conceivably consider the therapeutic application of VEGF peptides to stimulate further penile vascular development as has been contemplated for other vascular insufficiency conditions [9, 23]. Likewise, use of VEGF expression vectors provides a novel gene therapeutic approach for the curative treatment of erectile dysfunction, an approach that is being contemplated for other gene products involved in the response [47, 48]. By identifying the predominant angiogenic peptides naturally expressed in the erectile tissues of the penis, this goal is one step closer.

References

1. Impotence. NIH consensus statement 1992; 10(4):1–31.
2. Christ G J. The penis as a vascular organ. Urol Clin North Amer 1995; 22(4):727–745.
3. Karadeniz T, Topsakal M, Aydogmus A, Gulgun C, Aytekin Y, Basak D. Correlation of ultrastructural alterations in cavernous tissue with the clinical diagnosis vasculogenic impotence. Urol Int 1996; 57(1):58–61.
4. Nehra A, Hall S J, Basile G, Bertero E B, Moreland R, Toselli P, de las Morenas A, Goldstein I. Systemic sclerosis and impotence: a clincopathological correlation. J Urol 1995; 153(4):1140–1146.
5. Aydos K, Baltaci S, Saglam M, Tanyolac A, Anafarta K, Beduk Y, Gogus O. Ultrastructual changes of corpora cavernosa in vascular erectile dysfunction. Int Urol Nephrol 1996; 28(3):375–385.
6. Nehra A, Goldstein I, Pabby A, Nugent M, Huang Y H, de las Morenas A, Krane R J, Udelson D, Saenz de Tejada I, Moreland R B. Mechanisms of venous leakage; a prospective clinicopathological correlation of corporeal function and structure. J Urol 1996; 156(4):1320–1329.
7. Soker S, Takashima S, Miao H Q, Neufeld G, Klagsbrun M. Neuropilin-1 is expressed by endothelial and tumor cells as an isoform-specific receptor for vascular endothelial growth factor. Cell 1998; 92:735–745.
8. Ware J A, Simons M. Angiogenesis in ischemic heart disease. Nat Med 1997; 3(2):158–164.
9. Harada K, Friedman M, Lopez J J, Wang S Y, Li J, Prasad P V, Pearlman J D, Edelman E R, Sellke F W, Simons M. Vascular endothelial growth factor administration in chronic myocardial ischemia. Am J Physiol 1996; 270 (5/2) :H1791–1802.
10. Tusurumi Y, Murohara T, Krasinski K, Chen Witzenbichler B, . Kearney M, Couffinhal T, Isner J M. Reciprocal relation between VEGF and NO in the regulation of endothelial integrity. Nature Med 1997; 3(8):879–886.
11. De Jong J S, van Diest P J, van der Valk P, Baak J P. Expression of growth factors, growth-inhibiting factors, and their receptors in invasive breast cancer. II: Correlation with proliferation and angiogenesis. J Pathol 1998; 184(1):53–57.
12. Slavin J. Fibroblast growth factors: at the heart of angiogenesis. Cell Biol International 1995; 19(5) :431–444.
13. Battler A, Scheinowitz M, Bor A, Hasdai D, Vered Z, Di Segni E, Varda-Bloom N, Nass D, Engelberg S, Eldar M, Belkin M, Savion N. Intracoronary injection of basic fibroblast growth factor enhances angiogenesis in infarcted swine myocardium. JACC 1993; 7:2001–2006.
14. Jensen R L. Growth factor-mediated angiogenesis in the malignant progression of glial tumors: a review. Surg Neurol 1998; 49(2):189–195.
15. Conn G, Bayne M L, Soderman D D, Kwok P W, Sullivan K A, Palisi T M, Hope D A, Thomas K A. Amino acid and cDNA sequences of a vascular endothelial cell mitogen that is homologous to platelet-derived growth factor. Proc Natl Acad Sci 1990; 87:2628–2632.
16. Risau W, Flamme I. Vasculogenesis. Annu Rev Cell Dev Biol 1995; 11:73–91.
17. Relf M, LeJeune S, Scott PAE, Fox S, Smith K, Leek R, Moghaddam A, Whitehouse R, Bicknell R, Harris A L. Expression of the angiogenic factors vascular endothelial cell growth factor, acidic and basic fibroblast growth factor, tumor growth factor (-1, platelet-derived endothelial cell growth factor, placenta growth factor, and pleitrophin in human primary breast cancer and its relation to angiogenesis. Cancer Res 1997; 57:963–969.
18. Breier G, Albrecht U, Sterrer S, Risau W. Expression of vascular endothelial growth factor during embryonic angiogenesis and endothelial cell differentiation. Development 1992; 114:521–532.
19. Mack C A, Magovern C J, Budenbender K T, Patel S R, Schwarz E A, Zanzonico P, Ferris B, Sanborn T, Isom P, Isom O W, Crystal R G, Rosengart T K. Salvage angiogenesis induced by adenovirus-mediated gene transfer of vascular endothelial growth factor protects against ischemic vascular occlusion. J Vasc Surg 1998; 27(4) :699–709.
20. Takeshita S, Weir L, Chen D, Zheng L P, Riessen R, Bauters C, Symes J F, Ferrara N, Insner J M. Therapeutic angiogenesis following arterial gene transfer of vascular endothelial growth factor in a rabbit of hind limb ischemia. Biochem & Biophys Res Commun 1996; 227 (2):628–635.
21. Mulhauser J, Merrill M, Pili R, Maeda H, Bacic M, Bewig B, Passaniti A, Edwards N, Crystal R, Capogrossi M. VEGF 164 expressed by a replication-deficient recombinant adenovirus vector induces vasculogenesis in vivo. Circul Res 1995; 77:1077–1086.
22. Baffour R, Berman J, Garb J, Sang W R, Kaufmann J, Friedmann P. Enhanced vasculogenesis and growth of collaterals by in vivo administration of recombinant basic fibroblast growth factor in a rabbit model of acute lower limb ischemia: dose-response effect of basic fibroblast growth factor. J Vasc Surg 1992; 16(2):181–191.
23. Takeshita S, Zheng L P, Brogi E, Kearney M, Pu L Q, Bunting S, Ferrara N, Symes J, Isner J M. Therapeutic angiogenesis. A single intraarterial bolus of vascular endothelial growth factor, augments revascularization in a rabbit ischemic hind limb model. J Clin Invest 1994; 93(2):662–670.
24. Isner J M, Walsh K, Symes J F, Brogi E, Jurayi D. Arterial gene therapy for therapeutic vasculogenesis in patients with peripheral artery disease. Circulation 1995; 91:2687–2692.
25. Klein L T, Miller M I, Buttyan R, Raffo A J, Burchardt M, Devris G, Cao Y C, Olsson C, Shabsigh R. Apoptosis in the rat penis after penile denervation. J Urol 1997; 158:626–630.

26. Chomczynski P, Sacchi N. Single step method of RNA isolation by acid guanidinum thiocyanate-phenol-chloroform extraction. Anal Biochem 1987; 162(1): 156–159.
27. Sensibar J A, Sutkowski D M, Raffo A, Buttyan R, Griswold M D, Sylvester S R, Kozlowski J M, Lee C. Prevention of cell death induced by tumor necrosis factor alpha in LNCaP cells by overexpression of sulfated glycoprotein-2 (clusterin). Cancer Res 1995; 55(11) :2431–2437.
28. Bacic M, Edwards N A, Merrill M J. Differential expression of vascular endothelial growth factor (vascular permeability factor) forms in rat tissues. Growth Factors 1990; 12:11–15.
29. Wei M H, Popescu N C, Lerman M I, Merrill M J, Zimonjic D B. Localization of the human vascular endothelial factor gene, VEGF, at chromosome 6p12. Hum Genet 1996; 97:794–797.
30. Holliday R, Murray V. Specificity in splicing. Bioessays 1994; 16(10):771–774.
31. Smith C W J, Patton J G, Nadal-Ginard B. Alternative splicing in the control of gene expression. Annu Rev Genet 1989; 23:527–577
32. Houck K A, Ferrara N, Winer J, Cachianes G, Li B, Leung D W. The vascular endothelial growth factor family: identification of a fourth molecular species and characterization of alternative splicing of RNA. Mol Endo 1991; 5(12):1806–1814.
33. Houck K A, Leung D W, Rowland A M, Winer J, Ferrara N. Dual regulation of vascular endothelial growth factor-bioavailability by genetic and proteolytic mechanisms. J Biol Chem 1992; 267(36):26031–26037.
34. Neufeld G, Cohen T, Gitay-Goren H, Poltorak Z, Tessler S, Sharon R, Gengrinovitch S, Levi B Z. Similarities and differences between the vascular endothelial growth factor (VEGF) splice variants. Cancer & Metast Rev 1996; 15:153–158.
35. Bekmann R A, Merrill M J, Reinhold W C, Monacci W T, Saxena A, Clark W C, Robertson J T, Ali I U, Oldfield E H. Expression of the vascular permeability factor/ vascular endothelial growth factor gene in central nervous system neoplasma. J Clin Invest 1993; 91:153–159.
36. Wizigmann-Voos S, Breier G, Rissau W, Plate K H. Up-Regulation of vascular endothelial growth factor and it's receptors in von Hippel-Lindau Disease-associated and sporadic hemangioblaston-as. Cancer Res 1995; 55:1358–1364.
37. Harrison-Woolrych M L, Sharkey A M, Charnock-Jones D S, Smith S K. Localization and quantification of vascular endothelial growth factor messenger ribonucleic acid in human myometrium and leiomyomata. J Clin Endo & Metabol 1995; 80(6):1853–1858.
38. Cullunan-Bove A, Koos R D. Vascular endothelial growth factor/vascular permeability factor expression in the rat uterus: rapid stimulation by estrogen correlates with estrogen-induced increases in uterine capillary permeability and growth. Endocrinol 1993; 132(2):829–837.
39. Charnock-Jones D S, Sharkey A M, Rajput-Williams J, Burch D, Schofield J P, Fountain S A, Boocock C A, Smith S K. Identification and localization of alternately spliced mRNAs for vascular endothelial growth factor in human uterus and estrogen regulation in endcmetrial carcinoma cell lines. Biol Reprod 1993; 48(5) :1120–1128.
40. Poltorak Z, Cohen T, Sivan R, Kandelis Y, Spira G, Vlodavsky I, Keshet E, Neufeld G. VEGF 145, a secreted vascular endothelial growth factor isoform that binds to extracellular matrix. J Biol Chem 1996; 272(11) :7151–7158.
41. Cheung C Y, Singh M, Ebaugh M J, Brace R A. Vascular endothelial growth factor gene expression in ovine placenta and fetal membranes. Am J Obstet Gynecol 1995; 173(3/1):753–759.
42. Anthony F W, Wheeler T, Elcock C L, Pickett M, Thomas E J. Short report: Identification of a specific pattern of vascular endothelial growth factor mRNA expression in human placenta and cultured placental fibroblasts. Placenta 1994; 15(5):557–561.
43. Redmer D A, Dai Y, Li J, Charnock-Jones D S, Smith S K, Reynolds L P, Moor R M. Characterization and expression of vascular endothelial growth factor (VEGF) in the ovine corpus luteum. J Reprod & Fertil 1996; 108:157–165.
44. Mount S M. A catalogue of splice junction sequences. Nucleic Acids Research 1982; 10(2):459–472.
45. Te A E, Santarosa R P, Koo H P, Buttyan R, Greene L, Kaplan S A, Olsson C A, Shabsigh R. Neurotrophic factors in the rat penis. J Urol 1994; 152:2167–2172.
46. Sugihara T, Wadhwa R, Kaul S C, Mitsui Y. A novel alternatively spliced form of murine vascular endothelial growth factor, VEGF 115. J Biol Chem 1998; 273(5) :3033–3038.
47. Garban H, Marquez D, Magee T, Moody J, Rajavashisth T, Rodriguez J A, Hung A, Vernet D, Rajfer J, Gonzalez-Cadavid NF. Cloning of rat and human inducible penile nitric oxide synthase. Application for gene therapy of erectile dysfunction. Biol Reprod 1997; 56(4):954–963.
48. Christ G J, Rehman J, Day N, Salkoff L, Valcic M, Melman A, Geliebter J. Intracorporal injection of hSlo cDNA in rats produces physiologically relevant alterations in penile function. Am J Physiol 1998; 275(2PT1) :H600–H608.
49. Olofsson, B., et al. Proc. Natl. Acad. Sci. USA 1996; 93, 2576–2581.
50. Joukov, V., et al. EMBO J. 1996; 15(7), 1751.
51. Terman, B. I., Dougher-Vermazen, M. Cancer Metastasis Rev. 1996; 15(2), 159–163.
52. Neufeld, G., et al. Prog. Growth Factor Res. 1994; 5(1), 89–97.
53. Thomas, K. A., J. Biol. Chem. 1996; 271(2), 603–606.
54. Tischer, E., et al. J. Biol. Chem. 1991; 266(18), 11947–11954.

What is claimed is:

1. A method for increasing or maintaining the blood supply in the penis of a subject which method comprises injecting into the corpora cavernosa tissue of the subject's penis an amount of vascular endothelial growth factor effective to increase or maintain the blood supply in the subject's penis compared to the blood supply in the subject's penis prior to injecting the vascular endothelial growth factor, thereby increasing or maintaining the blood supply in the subject's penis.

2. A method for treating erectile dysfunction in a subject which method comprises injecting into the corpora cavernosa tissue of the subject's penis an amount of vascular endothelial growth factor effective to treat erectile dysfunction in the subject, thereby treating erectile dysfunction in the subject.

3. A method for increasing or maintaining the density of vascular structures in the penis of a subject which method comprises injecting into the corpora cavernosa tissue of the subject's penis an amount of vascular endothelial growth factor effective to increase or maintain the density of vascular structures in the subject's penis, thereby increasing or maintaining the density of vascular structures in the male subject's penis.

4. The method of claim 1, 2 or 3, wherein the vascular endothelial growth factor is VEGF-A 205/206, VEGF-A 188/189, VEGF-A 164/165, VEGF-A 144/145, VEGF-A 120/121, or VEGF-A 110.

5. The method of claim 1, 2 or 3, wherein the subject is human.

* * * * *